United States Patent [19]

Cardinale Fezler

[11] Patent Number: 5,834,027
[45] Date of Patent: Nov. 10, 1998

[54] INJECTION OF RHEA AND OSTRICH OILS IN ANIMALS

[76] Inventor: Donna L. Cardinale Fezler, Rte. 1, Box 97B, Jacksonville, Ill. 62650

[21] Appl. No.: 627,188

[22] Filed: Apr. 3, 1996

[51] Int. Cl.$^6$ .......................... A61K 35/12; A61K 45/00
[52] U.S. Cl. ....................... 424/522; 424/283.1; 424/520; 424/422; 424/526; 424/534; 424/574; 514/825; 514/899
[58] Field of Search .................................. 424/422, 522, 424/526, 534, 574, 283.1, 520; 514/825, 899

[56] References Cited

U.S. PATENT DOCUMENTS

| 5,431,924 | 7/1995 | Ghosh et al. ............................ 424/522 |
| 5,472,713 | 12/1995 | Fein et al. ............................... 424/522 |

OTHER PUBLICATIONS

Noble et al (1996) Comp. Biochem. Physiol. vol. 113B, No. 4, pp. 753–756.

Davies, P., D.E. MacIntyre: Prostaglandins and Inflammation. In: Gallin, J., M. Goldstein, R. Snyderman, ed. Inflammation: Basic Principles and Correlates, Second ed. New York: Raven Press, Ltd., 1992, 123–138.

Lam, B.K., K.F. Austen: Leukotrienes: Biosynthesis, Release, and Actions. In: Gallin, J., M. Goldstein, R. Snyderman, ed. Inflammation: Basic Principles and Correlates, Second ed. New York: Raven Press, Ltd., 1992; 139–147.

Dearing, J.D.: Rubber Rheas Revisted. Ratite Marketplace, Feb. 24, 1994: 29–30.

Speer, B.L.: Fading Chick Syndrome. American Ostrich, Aug. 1994: 30–31, 82, 85–86.

Smith, C.A.: Ostrich chick surival presents challenge. JAVMA, vol. 203, No. 5: Sep. 1, 1993: 637–643.

Owen, R.K.: Fading Chick Syndrome. Multi–State Bird Conference, Nov. 6–7, 1993.

Affonso, O.R., M.F. Lemos, S.M. Simas, E. Mitidieri: Effect of large intraperitoneal doses of fatty acids on the rat bloood serum xanthine dehydrogenase activity. Acta Biologica et Medica Germanica, 1977; 36(7–8): 1191–2.

Osmundsen, H., K. Eliassen: Stimulation of Hepatic Polyamine Metabolism Following Intraperitoneal Injection of some Dietary Oils. Acta pharmacol et toxicol. 1986; 58: 25–30.

McGee, C.D., C.E. Greenwood, K.N. Jeejeebhoy: Blood and Tissue Tocopherol Levels in Rats following Intraperitoneally Adminstered Alpha–Tocopheryl Acetate. Journal of Parenteral and Enteral Nutrition, 1990; 14: 74–78.

Gilsdorf, R.B., R. Selby, P. Tillach: Systemic Appearance of Nutrients Placed into the Peritoneal Cavity. Journal of Parenteral and Enteral Nutrition, 1985; 9: 148–152.

Veech, R.L., W.L. Gitomer, M.T. King, R.S. Balaban, J.L. Costa, E.D. Eanes. The effect of short chain fatty acid adminstration on hepatic glucose, phosphate . . . Advances in Experimental Medicine & Biology, 1986; 194: 617–46.

Golden, M.H.N., D. Ramdath. Free radicals in the pathogenesis of kwashiorkor. Proceedings of the Nutrition Society, 1987; 46: 53–68.

Mayatepek, E., K. Becker, L. Gana, G.F. Hoffman, M. Leichsenring. Leukotrienes in the pathophysiology of kwashiorkor. The Lancet, 1993; 342: 958–60.

Marin, M.C., M.E. DeTomas, O. Mercuri, A. Fernandez, C.T. de Serres. Interrelationship between protein–energy malnutrition and essential fatty acid deficiency in nursing infants. Am J Clin Nutr, 1991; 53: 466–8.

Jackson, A.A. Blood glutathione in severe malnutrition in childhood. Transactions of the Royal Society of Tropical Medicine and Hygiene, 1986; 80: 911–913.

*Primary Examiner*—Paula K. Hutzell
*Assistant Examiner*—Khalid Masood
*Attorney, Agent, or Firm*—Grace J. Fishel

[57] ABSTRACT

A method of treating animals, particularly rhea and ostrich chicks with adipose depletion, by injection with an oil derived from rhea or ostrich adipose or by injection with an active component of the oil that increases anti-inflammatory capabilities and phospholipid formation.

10 Claims, 4 Drawing Sheets

INJECTION OF RHEA AND OSTRICH OILS IN ANIMALS

BACKGROUND OF THE INVENTION

1. Field of the Invention

The present invention relates to a method for improving the condition of animals by injection with rhea and ostrich oils or with active components extracted therefrom or with functionally equivalent synthetic mimics that affects prostaglandin activity, inhibits leukotriene formation and/or promotes phospholipid bond formation.

2. Brief Description of the Prior Art

Ratites (e.g., ostrich, rhea, emu, cassowary and kiwi) are flightless birds of the sub-class Neornithae and family Struthiondae, Rheidae, Dromaiidae, Casuariidae and Apterygidae, respectively. Ostrich and rhea are raised commercially in various countries but chick survivability remains an elusive goal and a tremendous obstacle to the successful translation of ratites from an exotic market to a commercially viable livestock market. There are excellent incentives for commercializing these birds, including a very lean, low-saturated fat meat and, with ostriches for example, a feed conversion ratio approximate twice that of beef, and a potential annual meat production 20 times that of beef, when measured by pound of breeder animal, due to their high egg production.

Although adult ostriches are very hardy, the chicks are quite fragile, with average industry mortality estimated at 50% of live hatched eggs. One often-quoted phrase in the ostrich industry is "Ostrich chicks just wake up every morning looking for a place to die!" The economic losses of chick mortality with Fading Chick Syndrome are enormous, not only financially, but also in terms of time and emotional frustration to the farmer caring for the sick birds.

The mortality rate of rhea chicks is also high, manifested by conditions called Fading Chick Syndrome and Rubber Rhea Syndrome. Highest mortality in rhea chicks occurs within the first two months of life, and once a chick begins to decline, it is difficult to reverse the trend (1). Failure to gain weight is a generally accepted indicator of Fading Chick Syndrome in ratite chicks (2). Other signs of Fading Chick Syndrome are that the chick is listless or stands around with its head rolled toward its back, does not eat, has diarrhea or constipation, has a blank stare or dull eyes, stands with eyes half closed or sits away from the other chicks. Birds with Rubber Rhea Syndrome are characterized by pliable bills, low blood phosphorus and leg abnormalities that do not respond to vitamin or mineral supplements, and affected birds die. Based on the literature, it is not known whether these birds suffer from a nutritional problem, malabsorption, anorexia or a disorder of kidney phosphorus resorption (3).

Birds with Fading Chick Syndrome or Rubber Rhea Syndrome often succumb to infections with Protozoa (*hexamita*, Trichomonas), *C. perfringens* and *E. coli*. Morbidity and mortality can be 100% of infected flocks. Impactions are often diagnosed when there is no other evidence of infection. At necropsy, the duodenum is usually inflamed if the bird dies acutely. In chronic cases, the inflammation extends throughout the entire small intestine and into the omentum and may have progressed to a necrotizing enteritis. Typically the dead animals have exhausted their visible fat stores and may show moderate to severe muscle wasting. Especially in the case of protozoa infections, even after successful treatment, recovering birds may develop permanently disabling leg rotations so that they must be destroyed anyway. Attempts have been made to prophylactically treat the flocks with anti-microbial agents but there are no reports of successful prevention mechanisms.

The present invention is focused on the injection of rhea and ostrich oils into ratites and other birds for the purpose of improving survivability. In general, however, it has application to the injection of rhea and ostrich oils into animals (including humans) for the purpose of improving the animal's condition, and to the injection of active components extracted from the oils or functionally equivalent synthetic mimics, affecting prostaglandin activity, inhibiting leukotriene formation and/or promoting phospholipid bond formation, thereby suppressing pathological immune response and increasing mitogenic activity.

DETAILED DESCRIPTION OF THE INVENTION

Figure 1A:
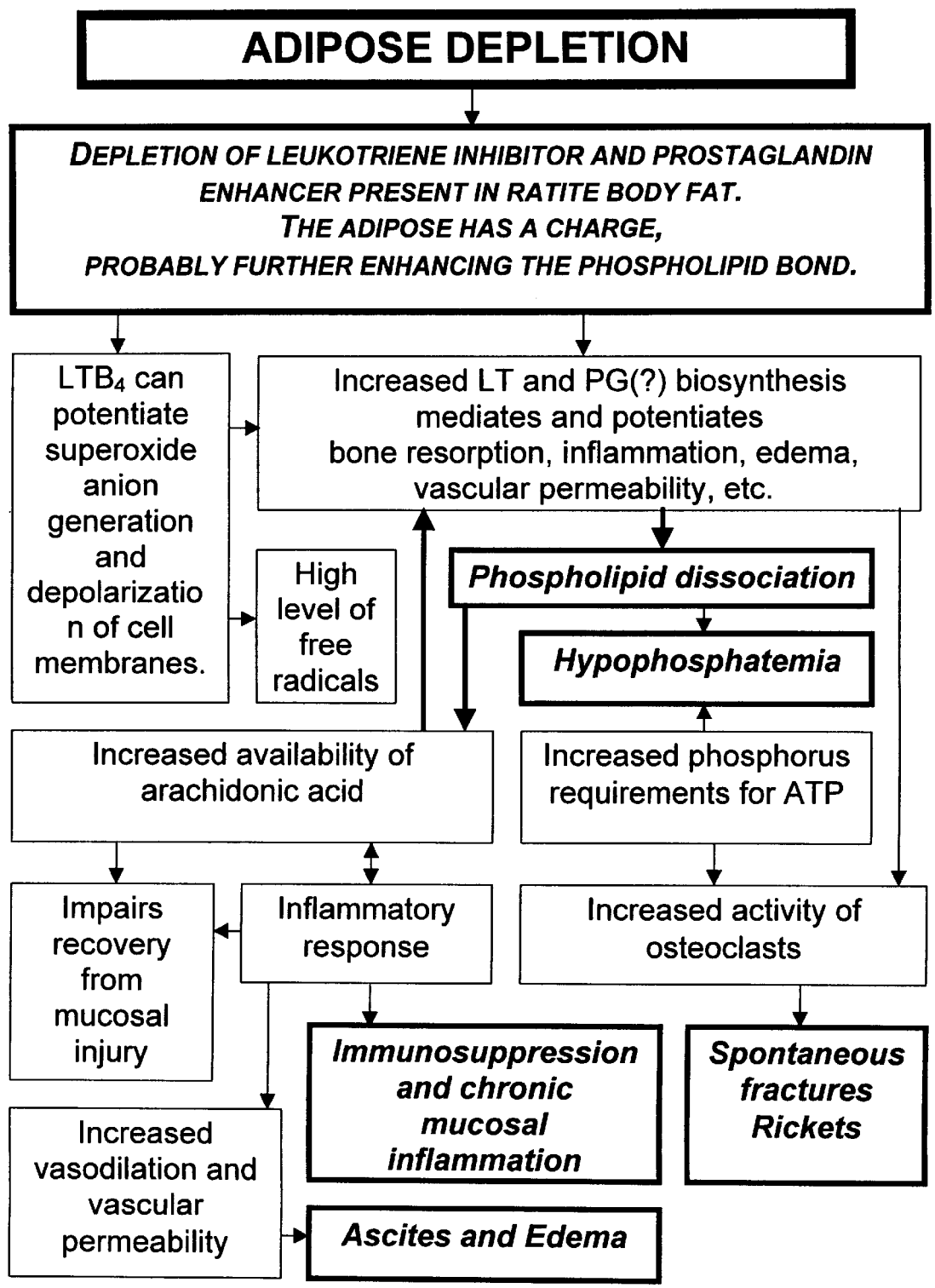
FIG. 1A–1C show a proposed mechanism explaining the sequence of events resulting from adipose depletion in rheas and ostriches.
Figure 1B:
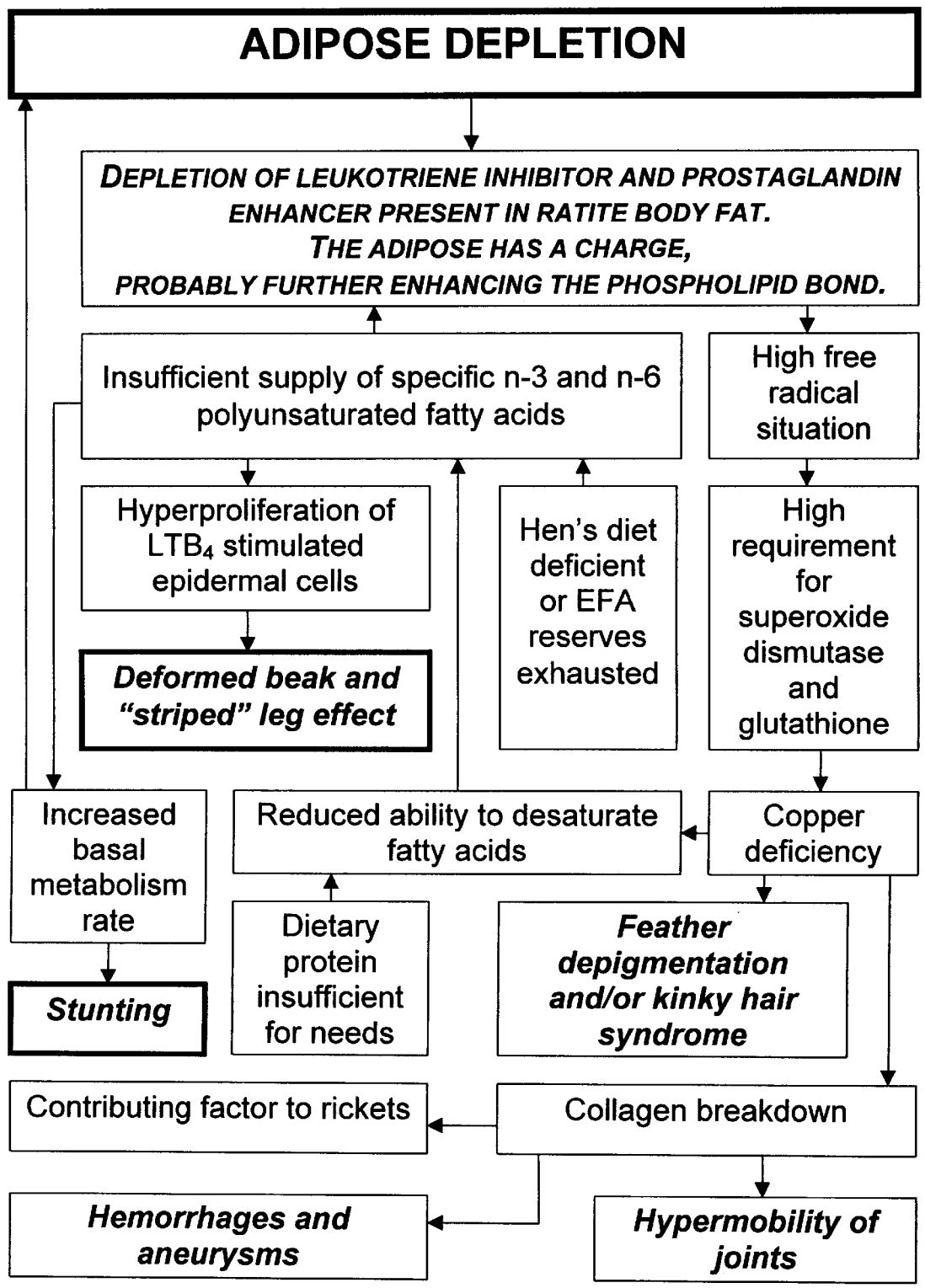
Figure 1C:
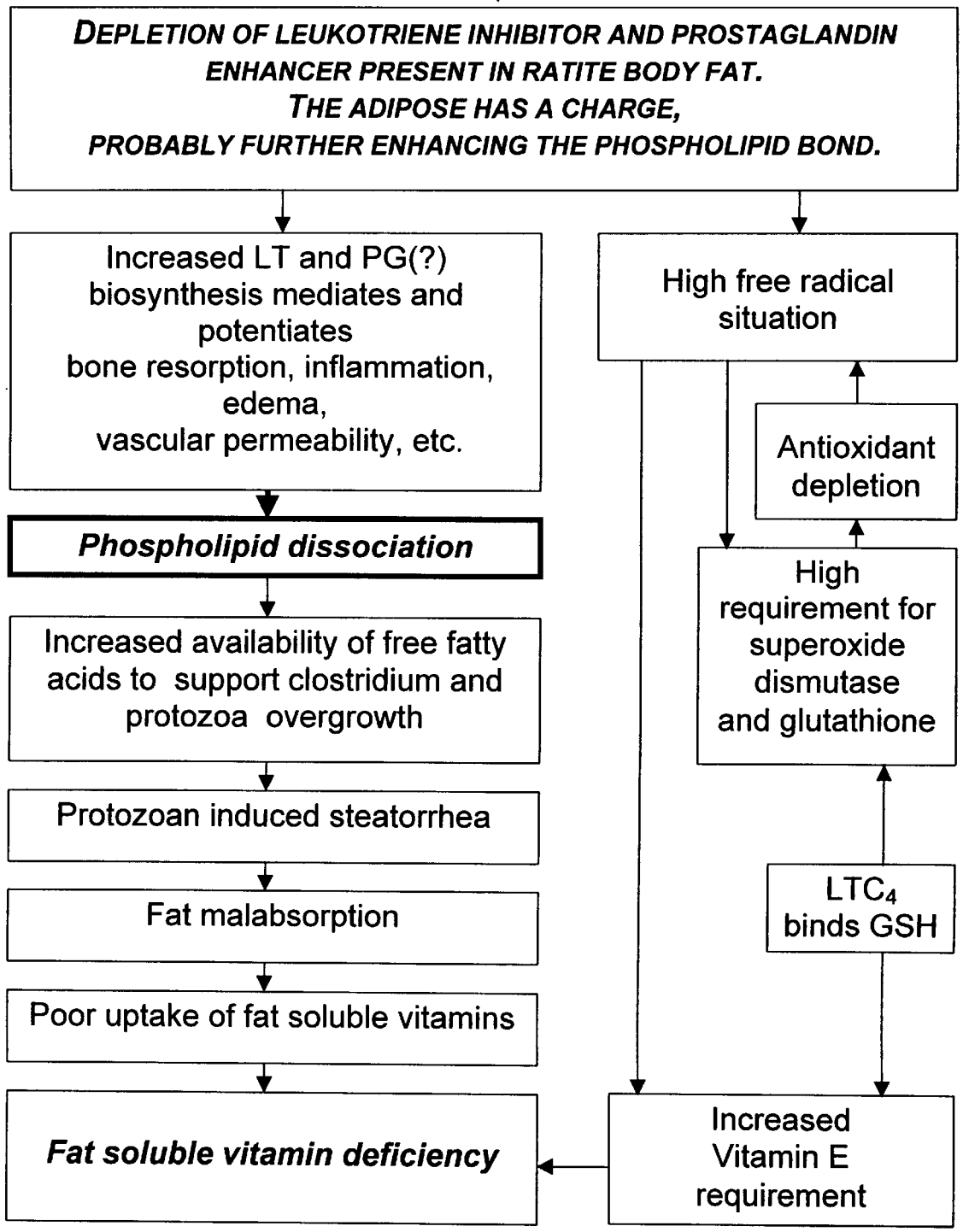

While not intending to be bound by any theory, it appears that Fading Chick Syndrome in rheas and ostriches and Rubber Rhea Syndrome and other similar conditions are the result of stress which causes the birds to deplete their store of adipose fat. A proposed sequence of events resulting from adipose depletion in rheas and ostriches is shown in FIG. 1A–1C.

Temperature extremes, lighting, noise, high microbial load, diet and change put the birds under stress. Biologically, stress causes the body to attempt to adapt to a situation temporarily that is not part of its genetically inherited "program". To do this, the body releases hormones, the hormones put an enormous drain on body functions and deplete available energy reserves. As will be further described hereinafter, without adequate reserves of adipose fat, the bird is unable to synthesize essential fatty acids necessary for survival even if fed a rich diet. Adipose fat also affects prostaglandin activity, inhibits leukotriene production and phospholipid bond formation, resulting in edema, ascites and other pathological immune responses. The lack of adipose fat also affects susceptibility to infectious diseases because of depressed mitogenic activity.

The energy drain from stress in rheas and ostriches is probably the single biggest factor in Fading Chick Syndrome and Rubber Rhea Syndrome. High levels of stress hormones promote bone demineralization, the release of fatty acids from the fat tissue, and impact the production and release of hormone-like substances called prostaglandins. Recognizing the earliest signs of stress is essential to stopping the overrunning mechanism. The difference between animals that die of Fading Chick Syndrome and animals that develop Rubber Rhea Syndrome is probably one of adaption. Rubber Rhea Syndrome may well be a normal adaption process for stress situations in which the body may be shunting the phosphorus and calcium from the bone to serve increased energy and signalling functions. This is important because low levels of prostaglandins actually promote bone development while high levels in the blood, which would occur when the chicks use up all their body fat, will cause bone demineralization, the end result of which is Rubber Rhea Syndrome.

The rhea has adipose fat that is rumored to be an anti-inflammatory topical remedy (4) although there is no documentation of its effect on humans or other animals. Adipose fat is generally considered to serve a storage, insulation or cushioning function. As is further described below, the physiological role of an anti-inflammatory adipose may provide rhea and ostrich chicks with a unique mechanism (5–12). In light of the high mortality encountered in breeding operations, the consistent depleted fat stores of afflicted animals (1,13–15), the anecdotal evidence of activity of the fat, and evidence of the significant role of fats or fatty acid metabolites (16) in nutrient absorption (12,17), inflammation (18,19) and bone remodeling (5–7,9,10), it was speculated that introducing fat from healthy birds into the peritoneal cavity of sick birds could affect weight gain with minimal risk to the chicks (20). Intraperitoneal injections of lipids have been found to be an effective route of delivery for nutritional support (21–25).

In accordance with the present invention, essential fatty acid deficiency, which may be manifested as Fading Chick Syndrome and Rubber Rhea Syndrome in rheas and ostriches, is treated by parenteral injection of oil obtained from rhea and ostrich adipose tissue. Injection increases anti-inflammatory capabilities and phospholipid bond formation. It also makes available body fat which can be released into the bloodstream. Suitable parenteral sites for injection include intramuscular, subcutaneous and intraperitoneal, the latter site being preferred when large volumes of oil are required. Any sick bird should be isolated from the flock and placed in a warm pen. Other sites may be preferred when the material affects prostaglandin activity, inhibits leukotriene formation and/or promotes phospholipid bond formation and has been extracted from the oil or synthetically made, in which case volume considerations do not dictate the site.

When the injection is made into the peritoneal cavity, care must be taken to avoid puncturing the air sacs which are very thin-walled, transparent bladders that originate from the bronchi on the ventral surface of the lung. While each ratite group has slightly different sized and shaped air sacs, basically they are located 1) in front of and within the thoracic inlet (cervical and clavicular air sacs), 2) attached below the lungs in the thorax (thoracic air sacs), and 3) within the abdomen (abdominal air sacs).

Suitable material for injection according to the present invention is preferably obtained from an adult bird, for example an adult rhea, has a higher concentration of long chain, unsaturated fatty acids than oil obtained from juveniles, and is therefore preferred as long chain (e.g., C20–C24). Unsaturated fatty acids play a role in the synthesis of essential fatty acids required for animal growth and are precursors of eicosanoids, very powerful, important, hormone-like substances. Essential fatty acids are constituents of phospholipids and glycerides in cell membranes and are precursors for synthesis of both linolenic and arachidonic acids. Arachidonic acid, in turn, is a precursor in the biosynthesis of prostaglandins, thromboxanes and leukotrienes, which are extremely active biological substances, with a wide spectrum of specific effects.

While rheas and ostriches are strikingly similar in their immune systems, etc., it is believed that oil obtained from adipose tissue of a rhea has a higher concentration of chemicals affecting prostaglandin activity, inhibiting leukotriene formation and promoting phospholipid bond formation than oil obtained, for example, from an ostrich. This is because ostriches and rheas evolved under quite different conditions in nature. The ostrich, a desert bird, lives in an arid environment with a fairly low microbial load and an inconstant supply of food. Many intestinal parasites will have a difficult time surviving under desert conditions. In contrast, a rhea is exposed to a much higher microbial load and a constant food supply in its natural habitat in South America. These factors have affected the ultimate design of the birds and may be a significant reason why rheas have evolved adipose fat with a higher degree of bioactivity. In view of the above, rhea oil is preferred for use in the present invention.

The preference of rhea oil over ostrich oil is consistent with anecdotal reports of persons using rhea and ostrich oils as folk remedies. It is speculated that rhea oil is more effective topically because the fat more effectively inhibits the production of leukotrienes. This inference is bolstered by the observation that one of the symptoms of kwashiorkor is edema which can be produced by the actions of the inflammatory agents, leukotrienes. Thus, rheas's fat may inhibit the production of the leukotrienes, not only in the bird but on human skin as well. When birds lose their body fat, the rhea chicks have no protection against the inflammatory agents, leukotrienes. Rhea oil contains eicosanoids that may play a pivotal role not only in the inflammation of the human disorders that appear to be relieved by the application of rhea oil, but also in the disease process of the birds. It is likely the rhea's special body fat is an evolutionary adaption to help keep the bird aline in times of stress. Hence Rubber Rhea Syndrome may be an adaption to stress related problems that gives baby rheas more time to try to overcome the problems than the baby ostrich has. We see this adaption that delays death as Rubber Rhea Syndrome, causing skeletal deformities in rheas prior to ultimately killing them, whereas in baby ostriches death occurs quicker, usually without the intermediate skeletal deformity step.

It appears that oil obtained from rheas and ostriches may be injected into birds of a different family or even animals of a different species. The amount injected and the frequency of the injection can be determined by those skilled in the art based on the physiological response of the animal undergoing treatment.

Rhea and ostrich oil is rendered and refined from adipose tissue, which may be taken, for example, from the Rhea Americana, or Common Rhea. The adipose is mainly deposited around the stomach and intestine, across the rump, and on both sides of the bowl-like sternum or breast bone. Small quantities can be found adjacent to most muscles. Rheas hatching have about 3 cc of fat distributed over the sternum, stomach, and rump. Typically, with current commercial nutrition programs, males do not begin to build fat stores until 12 months of age, and there is a marked increase in fat after sexual maturity. Fat harvested ranges from 3–15 pounds per yearling male, and is usually about 10% of body weight.

Rendering the adipose at home is best done in a microwave, followed by filtering it through a coffee filter to remove any organic matter which would support microbial growth, and storing it in the freezer. The resultant product is white, nearly odorless but not injectable. Rendering the product in a crockpot will overcook it, producing a yellow oxidized oil which is actually in the beginning stages of rancidity or oxidation caused by extended overheating of the oil.

Figure 2:
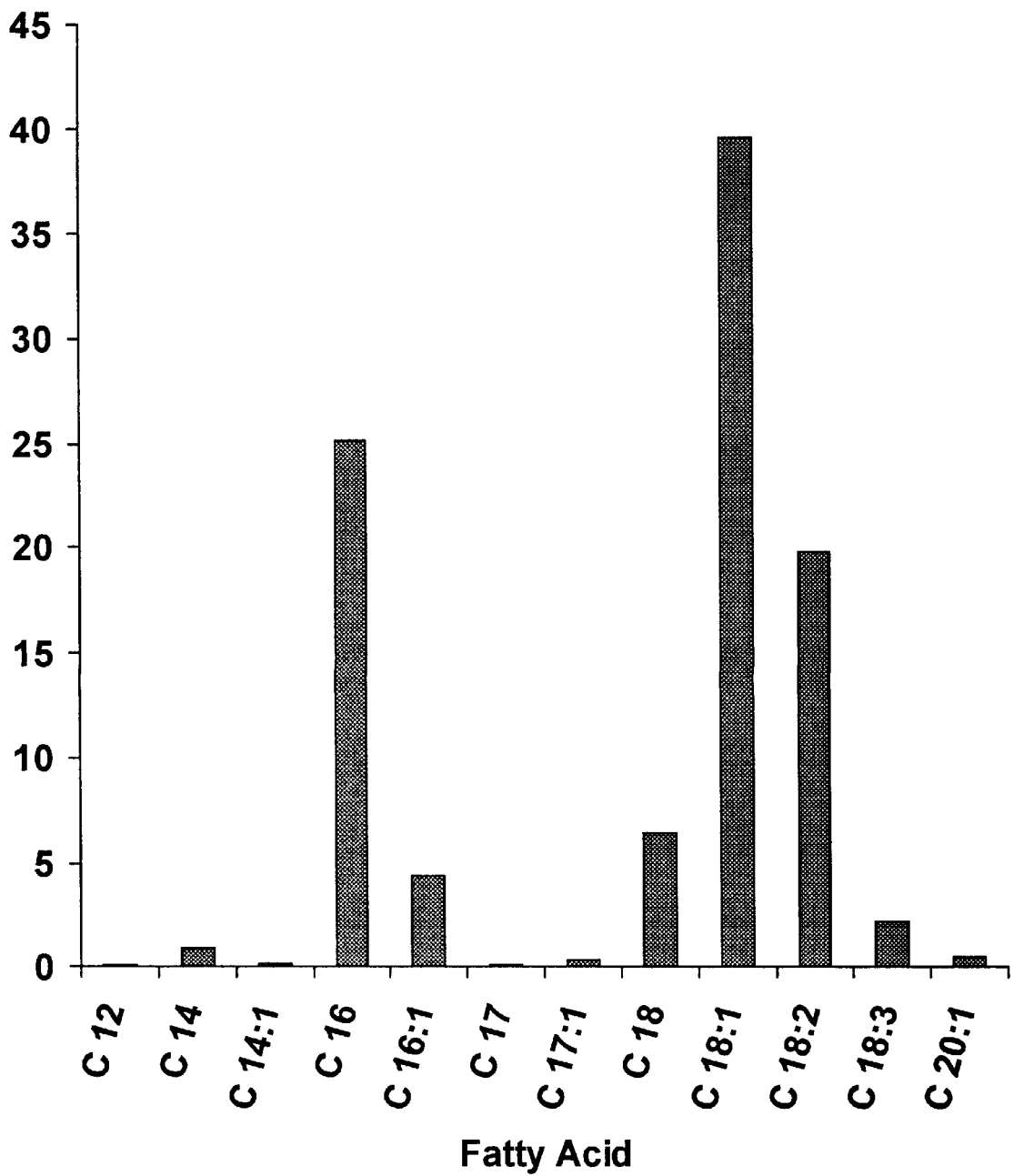
FIG. 2 is a fatty acid profile of refined, pharmaceutical grade, rhea oil.

To produce refined rhea oil, suitable for injection through a syringe, the rendered oil is heated to 160 degrees F. 1–2% USP diatomaceous earth is added by weight to the preheated oil and the oil is held at 200 degrees F., under vacuum and with agitation, for 5 minutes. The oil is vacuum filtered twice to remove all the bleaching earth and to separate the solid fat from the pure oil. The refined oil is then cooled in stages to 98 degrees for 24 hours, 74 degrees for 24 hours, and 60 degrees for 24 hours. A GLC fatty acid profile of the refined rhea oil is shown in FIG. 2. The GLC fatty acid profile for the clear oil and for the material left on the vacuum filter is essentially the same, except that the material on the filter may contain slightly more saturated fatty acids. The material on the filter is also biologically active. The fluid oil was sought so that it does not cloud when stored at room temperature and so that it is injectable through a syringe.

Commercial performance and refining standards can be developed. Those standards will define the minimum level for color, clarity, specific gravity, viscosity, refractive index, cloud test, peroxide value, melt point, iodine value, and fatty acids, to name several of the tests routinely done on oil.

According to current treatment, about 10 cc of prewarmed oil is injected intraperitoneally in chicks 5–10 pounds that are stunted or have rickets. Treatment is repeated as needed.

In some instances, it is advantageous to isolate that component of the oil affecting prostaglandin activity, inhibiting leukotriene formation and/or promoting phospholipid bond formation or to form a functionally equivalent synthetic material for injection. It will also be understood that in some instances, it may be advantageous to administer the oil or its above-mentioned active components with other materials, depending on the condition being treated. For example, the oil might be used as an adjuvant oil for vaccinations to alleviate the risk of inflammatory response. It could be used as a synergistic adjunct that can accentuate and accelerate the action of antibiotics, injectable or otherwise, by inhibiting the autoinflammatory response, potentially accelerating the defensive immune response. Other proposed uses include as an injectable alternative or adjunct to steroids in the management of rheumatic and collagen diseases. It may be used as an injectable alternative in cases where steroids are contraindicated, including but not limited to systemic fungal infections, adrenocorticoid hypersensitivity, immune deficiencies, GI ulceration, renal disease, hypertension, osteoporosis, diabetes mellitus, thromboembolic disorders, seizures, myasthenia gravis, congestive heart failure, tuberculosis, hypoalbuminemia, hypothyroidism, cirrhosis of the liver, emotional instability, hyperlipidemia, psychotic tendencies, glaucoma and cataracts. It may be used in cases where concomitant use of steroids and barbiturates, phenytoin, or rifampin may decrease the effect of the corticosteroids, or where corticosteroids increase the metabolism of isoniazis and salicylates causing hypoglycemia. Still other proposed uses include as an adjunct to chemotherapeutics to reduce toxic effects of cytotoxic agents on liver function and autoinflammatory agents, as an injectable leukotriene B4 inhibitor, as a synergistic adjunct to antihistamines, for the treatment of kwashiorkor and for the treatment of ascites of whatever cause.

The following examples illustrate the invention.

EXAMPLE 1

Six severely stunted rheas ranging in age from 5 to 7 months and weighing 1,900 to 5,300 g were housed in the same pen. Healthy birds of this age usually weigh between 9 and 18 kg. Rhea back and abdominal fat from commercially slaughtered adult male rheas was refined, bleached, deodorized and fractionated to a clear, liquid, injectable oil. Three birds received a single 10 cc rhea oil injection intraperitoneally, one of which developed sacculitis and died, the other two birds showed increased weight gain of 30.4% and 14.9%, 29 days post-injection. Three control birds had no rhea oil injected, although one control bird was given 2 cc *Clostridium perfringens* antitoxin type D and D. At Day 29, the uninjected controls showed weight losses of −5.9% and −11.8%, while the antitoxin treated control bird had a weight gain of 23.9%. The control birds with declining weights were subsequently injected with rhea oil intraperitoneally and showed weight gains of 30.2% and 14.8%, 29 days post-injection.

EXAMPLE 2

Sixteen rhea chicks, 20 to 24 days old, with poor weight gain (defined as less than 7 g per day), were randomly assigned to treated or untreated groups, with eight birds in each group. The treated group receive 3 to 5 cc refined rhea oil intraperitoneally.

Eight additional birds with pliable bills on manual examination were selected for a second treatment group, injected intraperitoneally with refined rhea oil and with phosphate supplement intramuscularly (4,26).

The birds in both treatment groups that did not show a sustained weight gain were reinjected with rhea oil. All birds were housed in a 30'×40' room, intermixed in raised runs and fed identical diets of half rabbit pellets, half 27% protein dog food supplemented with 3% kid milk replacer, 0.5% lecithin, 0.35% linseed, 1% cod liver oil and 100 IU vitamin E per kg with no antibiotics or other vitamin supplements added.

There was significant improvement in weight gain of the birds treated with rhea oil in the first treatment group, with an average daily weight gain of 12.5 g/day in the 25 day period following the initial injection, with total increase in weight of 63%. The birds gained an average of 17.6 g/day during the five days immediately following the first injection. The untreated birds died. The birds in the second treatment group with the pliable bills showed gains of 10.3 g/day, a 57% increase in weight. For comparison, normal, untreated, asymptomatic birds maintained a gain of 23.4 d/day, a weight increase of 46%.

EXAMPLE 3

Five rhea chicks ranging in age from 28 to 70 days were injected intraperitoneally with refined rhea oil, once a day for five days out of a seven day period, to establish if there were any observable effects of repeated administration of the oil. Doses ranged from 0.5 cc to 1 cc per 100 grams of body weight, with the highest dose over the period reaching 30 cc in a 1,100 g bird, or approximate 2.7% of body weight.

The birds selected for the experiment were compromised. They were thin with lumbar degeneration and all had poor feathering (dry, fluffy), and white faces lacking the characteristic blue coloration of a healthy bird. Birds in this condition generally die with the slightest stress. No antibiotics were administered to the birds.

The birds tolerated the procedures well with no immediate effects. Five days after the initial injection, the birds had noticeable changes in feathering. The dry fluffy feathering indicative of various nutritional disorders or deficiencies including essential fatty acids, protein, copper, and biotin had been alleviated. Some birds showed evidence of an excess of fatty acids, “greasy feathers” (darker color, limp, water repelling, matted). Since the birds themselves had a higher level of activity, this was not considered to be a deleterious effect. The blue coloration about the eyes, now believed to be an indicator of adequate levels of available copper in the birds, was markedly present ten days after the initial injection. Other than weight gain, no other effects were observed by the repeated introduction of oil into the peritoneal cavity of the rhea chicks. The only deleterious effect observed was a thickening of the skin at the abdomen which could be attributed to repeated injections. The thickening was not observed in birds observed 40 days later, indicating that it was not a permanent change.

EXAMPLE 4

A rhea hen, stressed by a pack of dogs running the perimeter of the pen during the previous night was offered for salvage, the owner expected it to die. The bird was thin and in seizure with its legs flailing and neck in corkscrew, lateral recumbency. Typically, this pose is indicative of hypoglycemia in young chicks and, if untreated, immediately precedes death. If treated with dextrose, death can be delayed, although as soon as the blood sugar falls to a critical level, the crisis resumes, and death is the usual outcome unless the underlying cause can be found. In ratites hypoglycemia is usually fatal.

The hen was transported for 25 minutes, while in seizure. She was treated with 7 cc of 50% by weight dextrose and 3 cc lactated ringers subcutaneously. Twenty cc of refined rhea oil was administered, 10 cc anterior to each leg. The bird was covered with towels for warmth. Within fifteen minutes she had assumed a standard resting pose and was alert and responsive. At this time she was placed under a heat lamp and towels in a barn with other birds.

Six hours post-injection, she was again in seizure. She was treated with 15 cc of 50% dextrose and 5 cc lactated ringers subcutaneously and 80 cc refined rhea oil injected subcutaneously, 5–10 cc per site at numerous sites along the bird's back and sides. Numerous sites were used to increase the absorption area and to minimize tissue disturbance caused by the volume being injected. She was placed under the heat lamp and towels for warmth. Again, within fifteen minutes she had calmed down and resumed the normal resting pose. One hour later she was crawling about on her hocks. Two hours later she was unsteadily walking. The next morning she appeared normal: eating, drinking and walking. She left the barn and rejoined the flock outside.

EXAMPLE 5

One cc of sterile canola, rhea or ostrich oil was injected subcutaneously into the backs of healthy mice. The responses of the mice were studies for behavioral responses beginning at five minutes post injection and continuing for 15 minutes. The behavioral differences are reported in the following table:

| Incident | Canola | Rhea | Ostrich | Control |
|---|---|---|---|---|
| Ear Scratches | 37 | 3 | 9 | 7 |
| Head Shaking | 12 | 5 | 8 | 0 |
| Total Incidents | 49 | 8 | 17 | 7 |

The mice were observed daily for five days. Only the canola injected specimen showed signs of edema beginning on Day 3. On Day 5 the canola injected mouse was euthanized. The site of injection was edematous, but showed no other gross indications of inflammation. The abdomen was also edematous. The rhea and ostrich oil injected mice showed no edema or other deleterious effects.

In view of the above, it will be seen that the several objects of the invention are achieved and other advantageous results attained. As various changes could be made in the above methods without departing from the scope of the invention, it is intended that all matter contained in the above description or shown in the accompanying drawings shall be interpreted as illustrative and not in a limiting sense.

REFERENCES

1. Angel C R. Personal Communication. 1995.
2. Speer B. Fading Chick Syndrome. American Ostrich 1994:30–31, 82–85.
3. Angel C R, Bermudez A. Serum vitamin D metabolites and chemistries from healthy rheas and rheas with "Rubber Rhea Syndrome". Association of Avian Veterinarians Session # 4040. Philadelphia, Pa., 1995.
4. Coutts M. Personal Communication. 1995.
5. Golde G. New clues into the etiology of osteoporosis: the effects of protaglandins (E2 and F2 alpha) on bone. Medical Hypotheses 1992;38(2):125–131.
6. Katz I A, Jee W S, Joffe, II, et al. Prostaglandin E2 alleviates cyclosporin A-induced bone loss in the rat. Journal of Bone & Mineral Research 1992;7(10):1191–1200.
7. Keck E, Schartl A, West T B, Kruskemper H L, Delling G. Influence of prostaglandins on electrolyte metabolism of human trabecular bone in vitro. Prostaglandins 1984;28(4) :455–67.
8. Ren W. Dzaik R. Effects of leukotrienes on osteoblastic cell proliferation. Calcified Tissue International 1991;49(3) :197–201.
9. Leonhardt A, Timmermannss G, Roth B, Seyberth H W. Calcium homeostasis and hypercalciuria in hyperprostaglandin E syndrome [see comments]. Journal of Pediatrics 1992;120(4 Pt 1):546–54.
10. Raisz L G, Pillbeam c c, Fall P M. Prostaglandins: Mechanisms of action and regulation of production in bone. Osteoporosis International 1993;3(Suppl 1):136–40.
11. Yamaguchi D T, Green J, Kleeman C R, Muallem S. Prostaglandins enhance parathyroid hormone-evoked increase in free cytosolic calcium concentration in osteoblast-like cells. Cell Calcium 1991:12(9):609–22.
12. Auguste L J, Lackner R, Ratner L, Stein T A, Bailey B. Prevention of stress-induced erosive gastritis by parenteral administration of arachidonic acid. Jpen: Journal of Parenteral & Enteral Nutrition 1990;14(6):615–7.
13. Bermudez A. Personal Communication. 1995.
14. Eldridge L. Personal Communication. 1995.
15. Hicks-Alldredge K. Personal Communication. 1994.
16. Bezard J, Blond J P, Bernard A, Clouet P. The metabolism and availability of essential fatty acids in animal and human tissues. Reproduction Nutrition, Development 1994;34(6):539–68.
17. Lo C, Paris P W, Clemens T L, Nolan J, Holick M F. Vitamin D absorption in healthy subjects and in patients in intestinal malabsorption syndromes. American Journal of Clinical Nutrition 1985:42(October):644–649.
18. Cunningham F. Lipid mediators in inflammatory skin disorders. Journal of Lipid Mediators 1990;2(2):61–74.
19. Ford-Hutchinson A W. Leukotrienes: their formation and role as inflammatory mediators. Federation Proceedings 1985;44(1 Pt 1):25–9.
20. Gilbertson J R, Gelman R A, Ove P, Coetzee M L. Inhibition of growth hepatomas 7777 and 7800 by, corn oil. Oncology 1977;34(2):62–4.
21. Gilsdorf R B, Selby R, Tillach P. Systemic appearance of nutrients placed into the peritoneal cavity. Jpen: Journal of Parenteral & Enteral Nutrition 1985;9(2):148–52.

22. McGee C D, Greenwood, C E, Jeejeebhoy K N. Blood and tissue tocopherol levels in rats following intraperitoneally administered alpha-tocopheryl acetate. Jpen: Journal of Parenteral & Enteral Nutrition 1990;14(1):74–8.

23. Osmundsen H, Eliassen K. Stimulation of hepatic polyamine metabolism following intraperitoneal injection of some dietary oils. Acta Pharmacologica et Toxicologica 1986;58(1):25–30.

24. Torres I J, Litterst C L, Guarino A M. Transport of model compounds across the peritoneal membrane in the rat. Pharmacology 1978;17(6):330–40.

25. Hidiroglou M, Charmley E. Comparative studies on bioavailability and tissue uptake of two intraruminally or intraperitoneally administered esters of alpha-tocopherol in sheep. American Journal of Veterinary Research 1991;52(4):640–2.

26. Dearing J. Personal Communication. 1994.

27. Richelsen B. Release and Effects of Prostaglandins in Adipose Tissue. Prostaglandins, Leukotrienes, and Essential Fatty Acids 1992;47:171–182.

What is claimed:

1. A method of injecting oil extracted from rhea or ostrich adipose, said method comprising injecting the oil into an animal in an amount sufficient to increase the animals's anti-inflammatory capabilities or phosphate bond formation.

2. A method of treating a rhea or ostrich with a condition of Fading Chick Syndrome or a rhea with Rubber Rhea Syndrome which comprises injecting an oil extracted from rhea or ostrich adipose into a bird with said condition in an amount sufficient to increase the level of fatty acids released into the bloodstream of the bird and to increase the bird's anti-inflammatory capabilities and phosphate bond formation.

3. The method of claim 2 wherein the oil is derived from rhea adipose.

4. The method of claim 2 wherein the oil is derived from adult rhea adipose.

5. The method of claim 2 wherein the oil is derived from adult male rhea adipose.

6. A method of treating a rhea or ostrich with adipose depletion which comprises injecting an oil derived from adult rhea adipose intraperitoneally into a bird with adipose depletion, said oil injected into the bird in an amount sufficient to increase the level of fatty acids released into the bloodstream of the bird and to increase its anti-inflammatory capabilities and phosphate bond formation.

7. The method of claim 6 wherein the oil has a fatty acid profile of FIG. 2.

8. The method of claim 6 wherein the oil is injected in amount between about 0.5 and 1.0 cc per kg of bird weight.

9. The method of claim 6 wherein the bird has air sacs and the injection avoids puncturing the air sacs.

10. The method of claim 6 wherein the bird is two months or less old.

* * * * *